United States Patent [19]

Nishio et al.

[11] Patent Number: 4,483,678
[45] Date of Patent: Nov. 20, 1984

[54] DENTAL IMPLANT FOR ATTACHMENT OF ARTIFICIAL TOOTH

[75] Inventors: Shinji Nishio; Kazuo Kondo, both of Aichi, Japan

[73] Assignee: NGK Spark Plug Co., Ltd., Aichi, Japan

[21] Appl. No.: 511,686

[22] Filed: Jul. 7, 1983

[30] Foreign Application Priority Data

Jul. 12, 1982 [JP] Japan ............................ 57-120800

[51] Int. Cl.³ ............................................. A61C 13/08
[52] U.S. Cl. .................................. 433/201; 128/92 C; 3/1.91
[58] Field of Search ........ 433/201; 128/92 C, 92 CA; 3/1.91

[56] References Cited

U.S. PATENT DOCUMENTS

| 4,146,936 | 4/1979 | Aoyzgi et al. | 128/92 C |
| 4,379,694 | 4/1983 | Riess | 433/201 |
| 4,424,037 | 1/1984 | Ogino et al. | 433/201 |

Primary Examiner—Robert Peshock
Attorney, Agent, or Firm—Sughrue, Mion, Zinn, Macpeak & Seas

[57] ABSTRACT

A dental implant for the attachment of a artificial tooth is described. This dental implant comprises a root portion to be embedded in bone and a top portion to be projected in the mouth, wherein the root portion comprises a high strength metal substrate, a ceramic or glass coating layer on the substrate, and a calcium phosphate coating layer on the ceramic or glass coating layer. The dental implant can be secured to a jaw bone and overcomes the problems involved in using conventional art dental implants, e.g., adverse influences of stainless steel.

9 Claims, 1 Drawing Figure

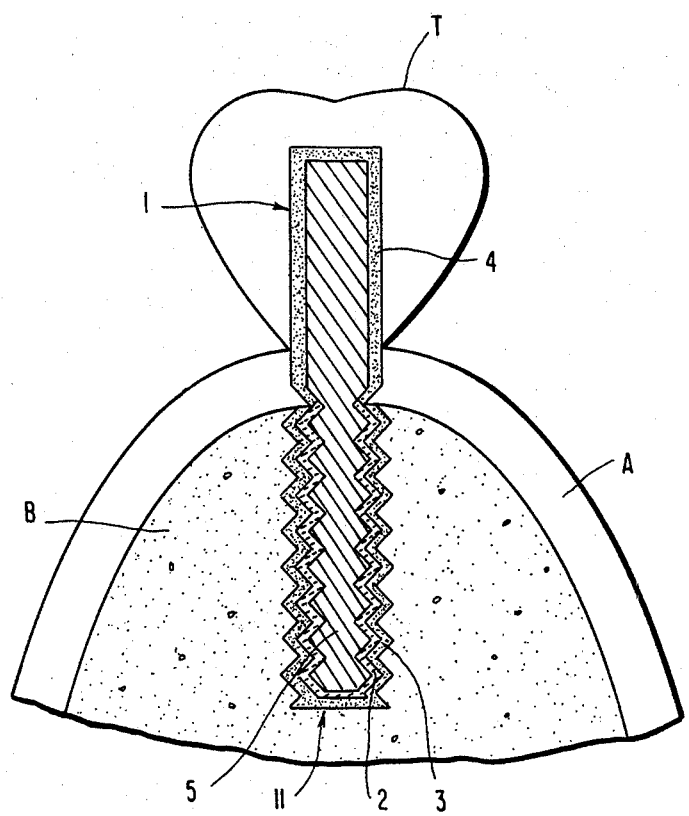

DENTAL IMPLANT FOR ATTACHMENT OF ARTIFICIAL TOOTH

FIELD OF THE INVENTION

The present invention relates to a dental implant for the attachment of an artificial tooth.

BACKGROUND OF THE INVENTION

Dental treatments comprising implanting a dental implant at a site where a tooth or teeth are missing, and, with the dental implant as a root, attaching an artificial tooth onto the top of the dental implant as a substitute for a natural tooth, have been clinically applied, and are known in the art.

Such dental implants are conventionally made of metals such as titanium and a cobalt/chromium/molybdenum alloy. In recent years, alumina ceramics have received increasing attention because of the superior in vivo characteristics thereof, and are now in widespread use.

Various techniques for implanting a dental implant are known; a very popular technique is as follows:

Mucosa at a site where a tooth or teeth are missing is peeled apart, a grooved or tapped hole conforming to the shape of the root portion of the dental implant is formed in a jaw bone, and thereafter, the dental implant is placed in the hole and the mucosa is closed. In accordance with another method, a dental implant is implanted in a tooth extraction hole.

These methods, however, suffer from the following disadvantages:

(1) Although metal has sufficiently high mechanical strength, it has poor affinity for human bones because of their different properties. Moreover, the metal can be ionized and eluded, exerting adverse influences on the human body.

(2) Although alumina ceramics are not harmful to human body, they are very hard compared with human bones and have poor affinity therewith. Therefore, when a dental implant of such alumina ceramics is used for a long period of time, a clearance is formed, resulting in damage to the jaw bone at the adhesion site.

It is described in Japanese patent application (OPI) No. 50194/79 (the term "OPI" as used herein refers to a "published unexamined Japanese patent application") that the surface of stainless steel can be coated with calcium phosphate to alleviate the foregoing problems. However, this calcium phosphate is gradually replaced in vivo by bone tissue and, finally, the bone and stainless steel may come into contact with each other.

There is also a danger of stainless steel's corroding over a long time period of use, and exerting adverse influences on the human body.

SUMMARY OF THE INVENTION

The present invention relates to a dental implant for the attachment of a artificial tooth, comprising a root portion to be embedded in bone and a top portion to be projected in the mouth from the tooth mucosa, wherein the root portion comprises a high strength metal substrate, a ceramic or glass (i.e., a material selected from the group consisting of ceramics and glass) coating layer on the metal substrate, and a calcium phosphate coating layer on the ceramic or glass coating layer.

In a preferred embodiment of the present invention, in order to increase an adhesion area between the ceramic or glass coating layer and a bone tissue, thereby improving the adhesion strength, the ceramic or glass coating layer is fabricated so as to have an irregular surface, which is threaded or horizontally grooved at a pitch of about 0.1~1 mm.

BRIEF DESCRIPTION OF THE DRAWING

The drawing is a cross-sectional view of a site wherein a dental implant in accordance with the present invention is implanted.

DETAILED DESCRIPTION OF THE INVENTION

The term "calcium phosphate" as used herein includes various types of calcium phosphate, e.g., from those compounds containing a large amount of calcium phosphate to those compounds called "apatite ceramics". Suitable examples include, e.g.: (1) high strength calcium phosphate as described in Japanese patent application (OPI) No. 56052/80 which is prepared by adding from 0.5 to 15% by weight of a calcium/phosphoric acid-based frit (Ca/P atomic ratio: 0.2/1 to 0.75/1) based on the weight of calcium phosphate component after calcined to powder composed mainly of calcium phosphate (Ca/P atomic ratio: 1.4/1 to 1.75/1) and, thereafter, melting the resulting mixture: (2) high strength calcium phosphate as described in Japanese patent application (OPI) No. 140756/80 (which corresponds to U.S. Pat. No. 4,376,168) which is prepared by adding from 0.5 to 15% by weight of alkali metal, zinc and/or alkaline earth metal oxide/phosphoric acid-based frit to the above-described calcium phosphate (Ca/P atomic ratio: 1.4/1 to 1.75/1), and thereafter calcining the resulting mixture; and high strength calcium phosphate as described in Japanese patent application (OPI) No. 80771/80 (which corresponds to U.S. Pat. No. 4,308,064), which is prepared by calcining a mixture of powder composed mainly of calcium phosphate and a calcium/phosphoric acid-based frit, and adding from 3 to 23% of $Y_2O_3$ as a reinforcing agent to the above-formed product.

The present invention will hereinafter be explained in more detail by reference to various preferred features and to the accompanying drawing.

Referring to the FIGURE, a dental implant 1 of the present invention has a dental root portion 11 at the lower portion thereof. The dental root portion 11 comprises a high strength metal substrate 5 made, e.g., of a nickel-chromium alloy stainless steel, a cobalt-chromiummolybdenum alloy stainless steel, titanium or the like, and a ceramic coating layer 2 on the metal substrate 5. The ceramic coating layer 2 is made of alumina, zirconia, spinel, forsterite or the like and is provided by known techniques such as chemical vapor deposition, physical deposition, and flame spraying. In order to increase the adhesion strength between the ceramic coating layer 2 and jaw bone B, the surface of the ceramic coating layer 2 is fabricated so as to be irregular, e.g., the metal substrate or, if desired, the ceramic or glass coating layer is threaded, transversely grooved, horizontally grooved or any other suitable treatment is used to increase the surface area of the ceramic coating layer 2. The ceramic coating layer 2 is then coated with a calcium phosphate coating layer 3.

A typical example of a method for production of a dental implant in accordance with the present invention is as follows:

A mixture of 20 kg of $CaCO_3$ and 14 kg of $P_2O_5$ was calcined at 1,300° C. for 2 hours to form a glass/crystal mixture of calcium phosphate which was in a half-molten state. The Ca/P atomic ratio of the mixture was about 1:1. The mixture was ground by means of a trommel (i.e., a ball mill) so that the proportion of particles having a size of $5\mu$ or less was 40%. The thus-ground calcium phosphate was then added to water with 1% of methyl cellulose dissolved therein and stirred to form a calcium phosphate slurry. A 15 mm portion of a nickel chromium alloy stainless steel substrate (2.5 mm in diameter and 25 mm in length) was threaded at a pitch of 1 mm, and thereafter provided with a $10\mu$ thick $\alpha$-$Al_2O_3$ coating layer by chemical vapor deposition. The substrate with the $\alpha$-$Al_2O_3$ coating layer provided thereon was then soaked in the above prepared calcium phosphate slurry, dried, and calcined in air at 700° C. to produce a dental implant with a calcium phosphate coating layer provided thereon.

Combustible powder having a particle size of from 20 to $500\mu$, such as carbon powder and an organic compound, for example, resin, polyethylene, foamed polyethylene, cellulose, vegetable fiber and grain powder, is incorporated into the calcium phosphate slurry in an amount of 5 to 60% by weight. The thus obtained mixture adheres to a ceramic or glass coating layer by means of dipping, brush coating or spraying, and then is sintered to provide a calcium phosphate coating layer having pores having an average diameter of from 20 to $500\mu$. Such a layer having pores has improved affinity for bones.

In implanting the dental implant of the present invention in a jaw bone, a mucosa A is cut and peeled away, a tapped hole conforming the shape of the dental implant is provided in a jaw bone B, and then, the dental root portion 11 of the dental implant is screwed in the tapped hole. A artificial tooth T is adhered onto the top portion of the implanted dental implant by means of an adhesive 4. The dental implant shows great affinity for the jaw bone because of the presence of the calcium phosphate coating layer. The calcium phosphate coating layer is gradually replaced by the bone. The replacement stops when the bone reaches the ceramic coating layer, and thus the bone does not come into contact with the stainless steel substrate. Therefore, even after a long period of time, the stainless steel does not exert adverse influences on human body. Moreover, since the ceramic coating layer has an irregular surface, the bone and the ceramic coating layer are bonded together over an increased surface area, and therefore the dental implant of the present invention can be used safely over a long period of time.

The surface of the ceramic coating layer may exist in a variety of forms, e.g., in the form of transverse grooves or horizontal grooves, or in a corrugated form, although it is threaded in the above-described embodiment. In addition, the close adhesion between the bone and the ceramic coating layer can be attained by producing a porous surface layer through proper adjustment of the particle size of, e.g., ceramic powder or glass powder, or of the flame temperature in flame spraying after deposition of ceramics. For example, ceramic bar or ceramic powder is molten at 2000° C. in case of alumina ceramic or at 1600° C. in case of zirconia ceramic with oxyacetylene flame and then the molten material is flame-coated at a pressure of 50 lb/inch² from the distance of 2 to 6 inches. Plasma jet flame can be used instead of the oxyacetylene flame.

While the invention has been described in detail and with reference to specific embodiments thereof, it will be apparent to one skilled in the art that various changes and modifications can be made therein without departing from the spirit and scope thereof.

What is claimed is:

1. A dental implant for the attachment of an artificial tooth, comprising a root portion to be embedded in bone and a top portion to be projected in the mouth from the tooth mucosa, wherein the root portion comprises a high strength metal substrate, a ceramic or glass coating layer on the metal substrate, and a calcium phosphate coating layer on the ceramic or glass coating layer.

2. A dental implant as in claim 1, wherein the ceramic or glass coating layer has an irregular surface.

3. A dental implant as in claim 1, wherein the ceramic coating layer is made of alumina, zirconia, spinel, or forsterite.

4. A dental implant as in claim 2, wherein the ceramic coating layer is made of alumina, zirconia, spinel, or forsterite.

5. A dental implant as in claim 1, wherein the calcium phosphate coating layer contains pores having an average diameter of from 20 to $500\mu$.

6. A dental implant as in claim 2, wherein the calcium phosphate coating layer contains pores having an average diameter of from 20 to $500\mu$.

7. A dental implant as in claim 3, wherein the calcium phosphate coating layer contains pores having an average diameter of from 20 to $500\mu$.

8. A dental implant as in claim 4, wherein the calcium phosphate coating layer contains pores having an average diameter of from 20 to $500\mu$.

9. A dental implant as in claim 1, wherein said calcium phosphate is an apatite ceramic.

* * * * *